(12) United States Patent
Samkov et al.

(10) Patent No.: US 6,569,197 B2
(45) Date of Patent: May 27, 2003

(54) HEART VALVE PROSTHESIS

(76) Inventors: Alexandr Vasilievich Samkov, ul. Generala Tuleneva, d. 1, kv. 13, Moscow 117465 (RU); Naum Abramovich Iofis, Lomonosovsky pr. d. 23, kv. 416, Moscow 117311 (RU); Andrej Vasilievich Agafonov, Smolnaya ul., d. 63, kv. 149, Moscow 125445 (RU)

( * ) Notice: Subject to any disclaimer, the term of this patent is extended or adjusted under 35 U.S.C. 154(b) by 0 days.

(21) Appl. No.: 09/893,227

(22) Filed: Jun. 27, 2001

(65) Prior Publication Data

US 2002/0022879 A1 Feb. 21, 2002

(51) Int. Cl.[7] .................................................. A61F 2/24
(52) U.S. Cl. ...................... 623/2.23; 623/2.28; 623/2.42
(58) Field of Search .............................. 623/2.2, 2.22, 623/2.23, 2.27, 2.28, 2.29, 2.3, 2.31–2.33

(56) References Cited

U.S. PATENT DOCUMENTS

| 4,274,437 | A | * | 6/1981 | Watts | 623/2.21 |
| 4,308,624 | A | * | 1/1982 | Klawatter | 623/2.32 |
| 4,406,022 | A | * | 9/1983 | Roy | 623/2.27 |
| 4,863,467 | A | * | 9/1989 | Bokros | 623/2.3 |
| 4,872,875 | A | * | 10/1989 | Hwang | 623/2.22 |
| 4,888,010 | A | * | 12/1989 | Bokros | 623/2.3 |
| 5,061,278 | A | * | 10/1991 | Bicer | 623/2.27 |
| 5,192,313 | A | * | 3/1993 | Budd et al. | 623/2.29 |
| 5,397,347 | A | | 3/1995 | Cuilleron et al. | |
| 5,653,750 | A | | 8/1997 | Cuilleron et al. | |
| 5,861,029 | A | * | 1/1999 | Evdokimov et al. | 623/2.26 |

FOREIGN PATENT DOCUMENTS

| RU | 2066984 | 9/1996 |
| RU | 2113191 | 6/1998 |

* cited by examiner

Primary Examiner—Danton D. DeMille
Assistant Examiner—Quang D. Thanh
(74) Attorney, Agent, or Firm—Anderson Kill & Olick; Eugene Lieberstein; Michael N. Meller

(57) ABSTRACT

The present invention relates to a heart valve prosthesis having an annular body with a pair of flanges, and a closing element in the form of two or three flaps mounted through bearings into the body's recesses with freedom to be rotated. The annular body has a constant height on a greater portion of a ring circle, and a number of ledges equal to that of the flaps. The ledges are provided with flap rotation limiters. The flaps have ascending and descending surfaces oriented to the direct and reverse flow of blood, a side edge and an edge for joining the other flap. The descending surface of a flap is flat and the ascending surface thereof is spherically concave. The flaps have the minimal thickness on an axis of symmetry at the joining edge. The axes of rotation of the three flap embodiment are arranged relative to each other at an angle of 60° thereby to form the sides of an equilateral triangle. For the valve with two flaps the flange facing the direct flow of blood is thickened. Recesses for bearings enter into the thickened flange with the recesses having a lateral cylindrical surface and a concave bottom.

10 Claims, 5 Drawing Sheets

HEART VALVE PROSTHESIS

TECHNICAL FIELD

The present invention relates to medical techniques and can be used in heart surgery for the replacement of damaged natural aortal and mitral human heart valves. The invention can also be put to use in replacing affected tricuspid and lung artery valves.

PRIOR ART

Known in the art is a heart valve prosthesis (U.S. Pat. No. 4,276,658, 1981) comprising an annular body with a pair of ledges on a surface facing a forward flow of blood, and two flaps which are provided with bearings on the side edges of each and every flap. The bearings hingeably enter into recesses on the interior surface of the body's ledges, which permits closing and opening the flaps by rotation. The recesses on the body of the prosthesis have a spherical bottom defined by two V-like rotation limiters, which are adapted to be operatively engaged, by lateral surfaces thereof, with the flap bearings. The interior surface of the body has two diametrically opposed flat portions.

With such a construction, arrangement of the rotation limiters of flaps directly in a hinge area, and contact of their lateral surfaces with flap bearings in open and closed positions do not practically make it possible to fully wash the lateral surfaces using both forward and reverse flows of blood. This results in the appearance of hyperemic zones, which facilitate the formation of blood clots.

The possibility of thrombosis is somewhat lowered with another construction of a heart valve prosthesis (U.S. Pat. No. 4,308,624, 1982). The valve is comprised of an annular body, a closing element of two flaps with bearings on the side edges of each flap. Each of the flaps has a respective ascending and a descending surface, oriented towards the forward and reverse flows of blood, a aide edge adapted to cooperate with the interior surface of the annular body, and an edge for joining the other flap. The bearings of flaps are arranged in the recesses on the interior surface of the body with freedom to be rotated between the closing/opening positions. The limiters of flap rotation are the internal projections of the body.

The flaps are bow-shaped in a cross-sectional area, and their descending surfaces facing, in a closed position, the reverse flow of blood are made concave. On the interior surface of the body at different levels thereof are provided two diametrically opposed flat portions. The bearings of flaps are spherical to be washed with blood in the best possible way. The recesses on the interior surface of the body have a semicircular cross-sectional area and are extended and inclined 70° to the plane perpendicular to the central line of the prosthesis. The rotation limiters are taken out of a zone of cooperation of the flap bearings with the recesses on the body's interior surface.

When a closing element is in an open position, because of concavity of the descending surfaces of flaps, a canal is formed therebetween for a forward flow of blood to pass therethrough, and along with this, the canal's width in the central portion of the prosthesis is maximal and diminishes towards the interior surface of the body, wherein are provided elongated recesses for flap bearings. Hydrodynamic investigations go to show that the structure of a direct flow in-between the flaps is not uniform. If in the plane perpendicular to that of the flaps, a flow is practically laminar and fills all of the section of the valve, then in the plane parallel to the edges for joining the flaps the laminar flow is observed only in the prosthesis's central portion while a spacious hyperemic zone is there in the area of hinges, which is increased further with said shape of implementation of the flaps. The slide of flaps, in opening and/or closing positions, along the extended recesses does not impede thrombosis because it does not remove the hyperemic zones and does not provide for washing the zones of cooperation of the flap bearings with the recesses. Besides this, the flap bearings may move in an asynchronous manner along an extended recess in closing/opening the valve, a factor that will lead to the prosthesis's unstable work expressed in the fluctuation of values of the forward and reverse flows of blood and in the difference of mechanical forces exerting an influence on the prosthesis's elements, which lowers reliability of its operation.

The embodiment of a rotation limiter in the form of ledges on the interior surface of the body improves the washing of the prosthesis with the blood, albeit reduces at the same time the prosthesis's flow section or—to be more exact—lowers its hemo dynamic effectiveness.

Many of the defects could not be overcome completely in both an artificial heart valve with flat petals (Patent GB 2,055,452, 1981) and in the construction of a valve with curved flaps (U.S. Pat. No. 5,397,347, 1995).

SUMMARY OF THE INVENTION

The invention, as being claimed and as set forth in the application, enables one to diminish the possibility of thrombosis by way of improving a washing step of heart valve prosthesis elements using the blood, by enhancing the reliability and hemo-dynamic effectiveness of the valve.

The prosthesis of a heart valve comprises an annular body with two flanges, and a closing element in the form of two or three flaps, which are mounted through bearings in the recesses of the body with a faculty of rotation. If the closing element has two flaps, their axes of rotation are parallel in the vicinity of the diametric plane of the valve. In this case the interior surface of the body about the entire periphery is cylindrical with no protrusions, that is the flow section of the annular body has a form of a circle and is not varied at different levels. The body has a constant height on a greater portion of a ring circle and ledges. The number of ledges is equal to that of the flaps. The ledges are provided with flap rotation limiters on the side facing the direct flow of blood. In the preferable embodiment, the ledges are W-shaped and their interior surface from the side of the direct flow of blood is inclined to the central axis of the body.

The flaps have ascending and descending surfaces facing a direct and a reverse flow of blood, respectively, a side edge for contact with the interior surface of the body, and an edge for joining the other flap. The descending surface of the flap, oriented towards the reverse flow of blood is flat while the ascending surface of the flap oriented towards the direct flow of blood is spherically concave. The least thickness of the flaps is on the axis of symmetry at the joining edge.

The recesses for bearings have a lateral cylindrical surface and a concave bottom. The flange turned to the direct flow of blood is preferably thickened, the recesses for bearings at least partially being gone into the thickened flange.

The recesses for bearings can be made in the form of a triad of communicating blind holes. which is comprised of the central and two side holes. And in the preferable embodiment, a radius of the central hole is greater than the radii of the side holes, and the depth of the central hole is greater than that of the side holes.

In case of a closing element having three flaps, each one have two joining edges obliquely converging towards the central axis of the body and, along with this, the axes of rotation of the flaps are arranged at an angle of 60° to form the sides of an equilateral triangle. In this case the interior surface of the body has the protrusions for the recesses for bearings to be made. This permits to fasten the flaps of the closing element to the annular body more reliable.

Preferable materials for making a heart valve prosthesis are pyrocarbon or titanium with a carbon-containing surface layer, in which a carbon content decreases gradually from the surface into the depth of the material of the body. A possibility of the latter being obtained just for artificial heart valves is described in patent RU 2109495, 1998.

BRIEF DESCRIPTION OF THE DRAWINGS

The invention will now be described in detail with reference to the accompanying drawings where.

PREFERRED EMBODIMENTS OF THE INVENTION

Figure 1:
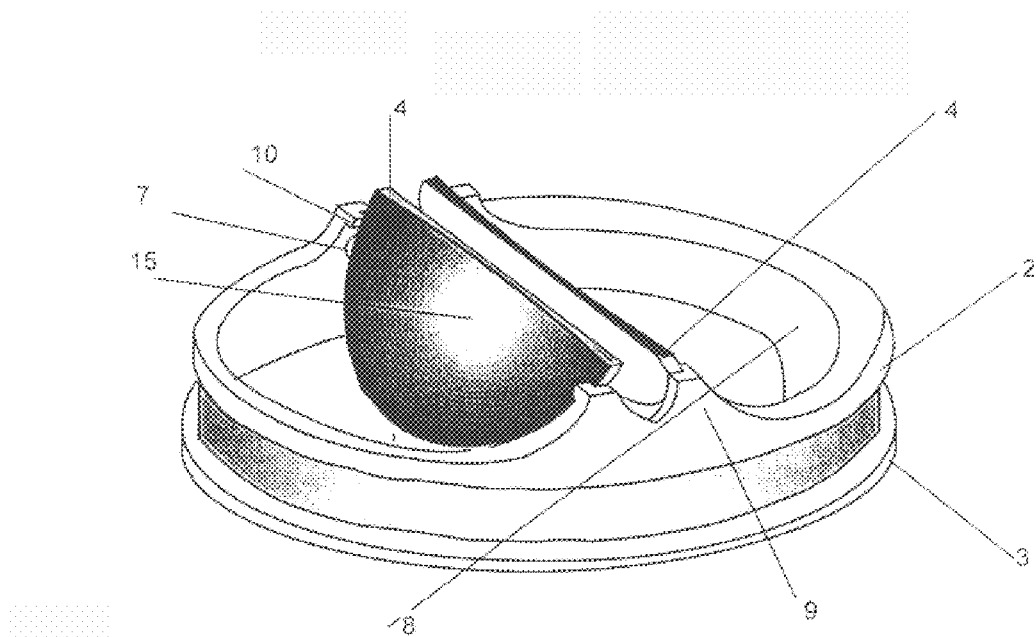
FIG. 1 shows an enlarged axonometric picture of a valve with a pair of flaps.

A heart valve prosthesis comprises an annular body 1 with a pair of flanges 2, 3, and a closing element in the form of two flaps 4 or three flaps 5, which are mounted through bearings 6 in recesses 7 of the body 1 with freedom to be rotated. In the embodiment with two flaps the interior surface 8 of the body 1 about the entire periphery is cylindrical with no protrusions, that is the flow section of the annular body 1 has a form of a circle and is not varied at different levels (FIG. 1). Body 1 has a constant height on a greater portion of a ring circle, and ledges 9, the number of ledges being equal to that of the flaps. Ledges 9 are provided with rotation limiters of the flaps 4 or 5. In the preferable embodiment, the ledges 9 are W-shaped and their interior surface from the side of the direct flow of blood is inclined towards the central axis of the body 1.

The flaps 4 and 5 have ascending and descending surfaces oriented towards a direct and a reverse flow of blood, respectively, a side edge 11 having a faculty of contact with the interior surface 8 of body 1, and an edge 12 (or edges 13) for joining the other flap 4 or 5. A descending surface 14 of flap 4, facing the reverse flow of blood is flat, and an ascending surface 15 of flap 4, facing the direct flow of blood is spherically concave. Flaps 5 have the corresponding shape of the descending and ascending surfaces. The minimal thickness of flaps 4 and 5 is on an axis of symmetry at the joining edge.

The flange 2 turned to the direct flow of blood is thickened in the preferable embodiment. The recesses 7 for bearings at least partially go into the thickened flange 2 and the recesses have a lateral cylindrical surface 16 and a concave bottom 17 (FIG. 4).

Figure 4:
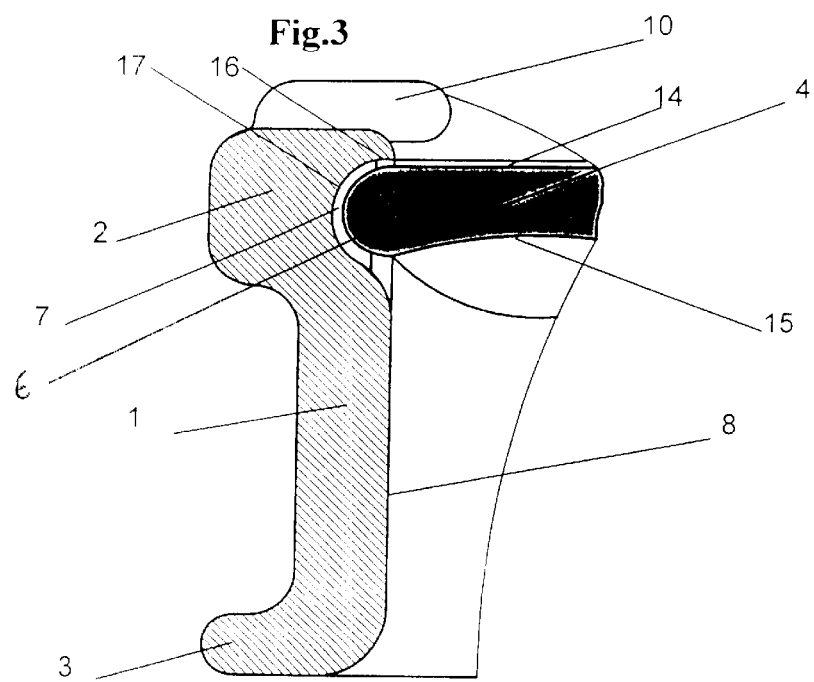
FIG. 4—arrangement of a flap bearing in a recess in a thickened flange of the body.
Figure 5:
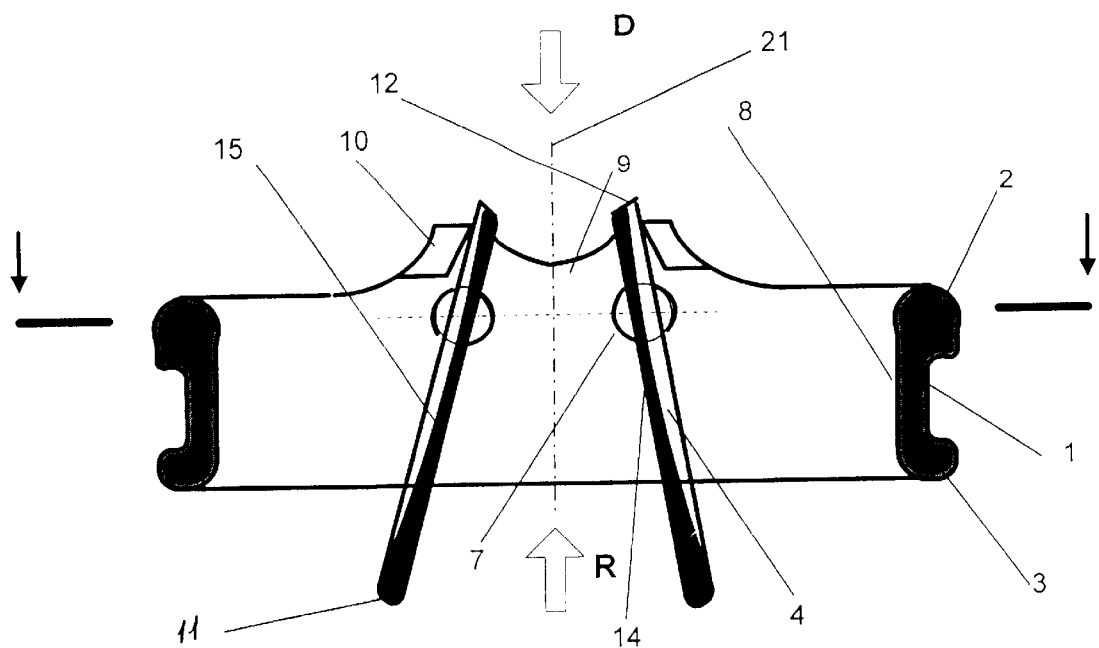
FIG. 5—view of a heart valve prosthesis in a diametric section, with flaps in an open position.

The recesses 7 for the bearings 6 at least partially go into the thickened flange 2 and the recesses 7 may have a lateral cylindrical surface 16 and a concave, for example, spherical bottom 17 (FIG. 4).

Figure 2:
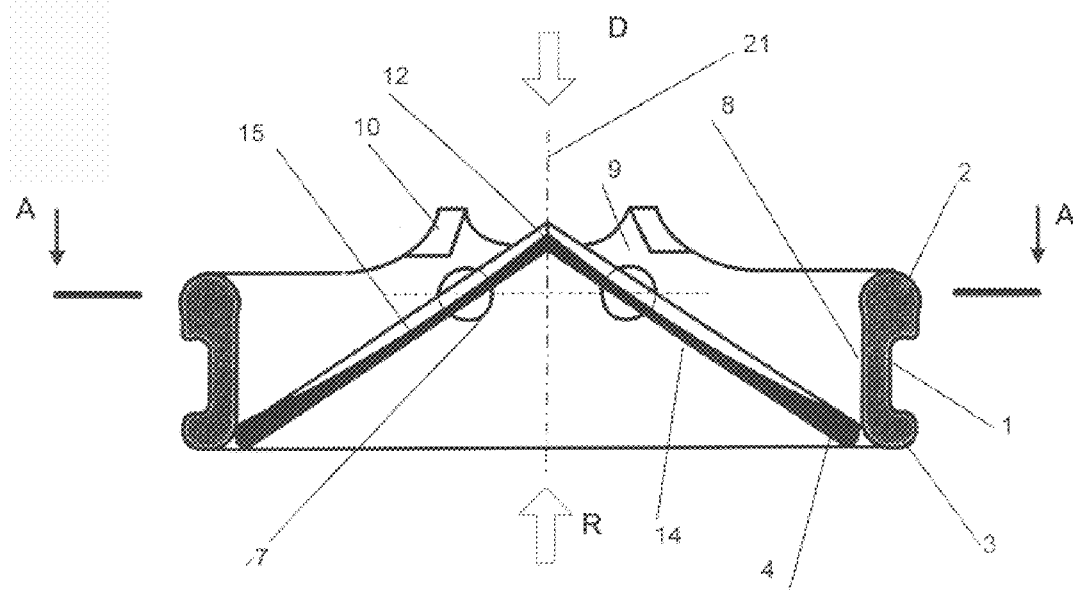
FIG. 2 shows a general view of a heart valve prosthesis in a diametric section; flaps are in a closed position.
Figure 3:
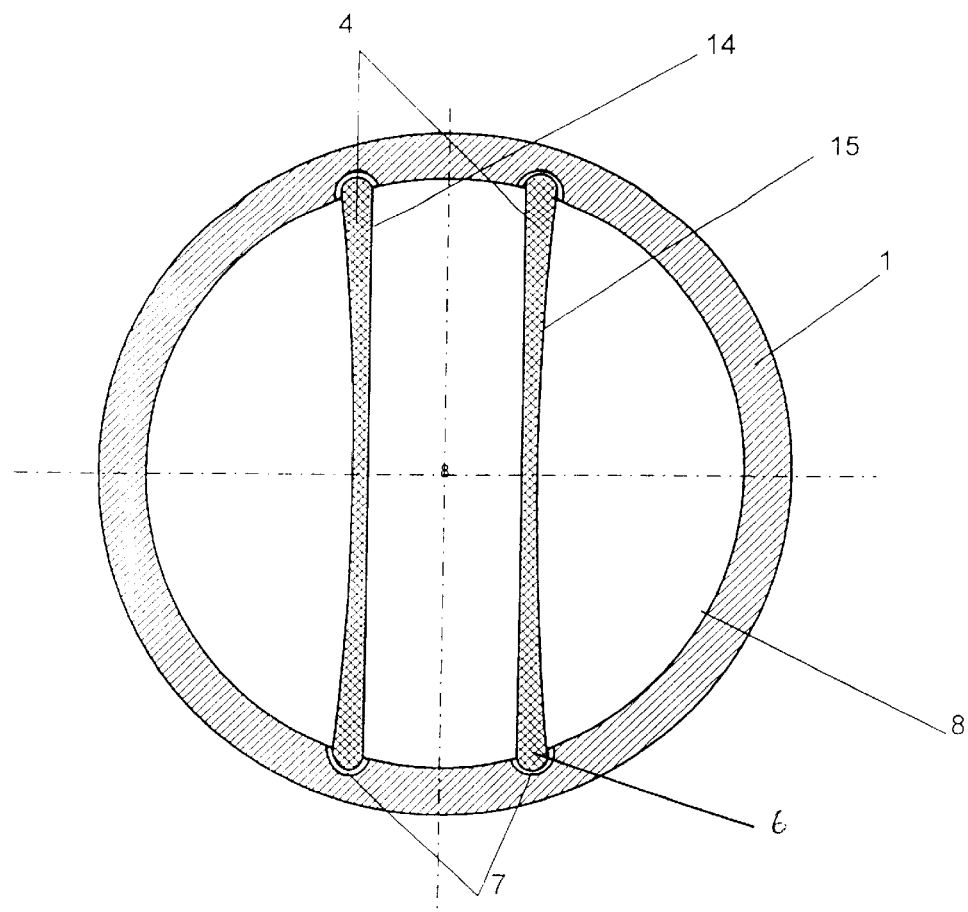
FIG. 3—a section of a valve prosthesis taken on the level of flaps rotation axes.
Figure 6:
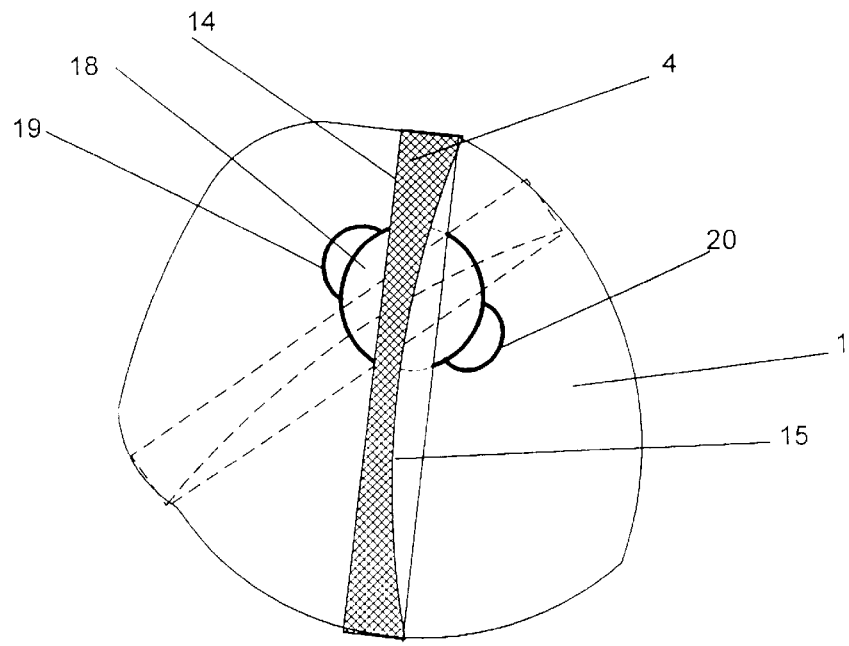
FIG. 6—a recess for flap bearings, which is implemented in the form of a triad of communicating blind holes.
Figure 7:
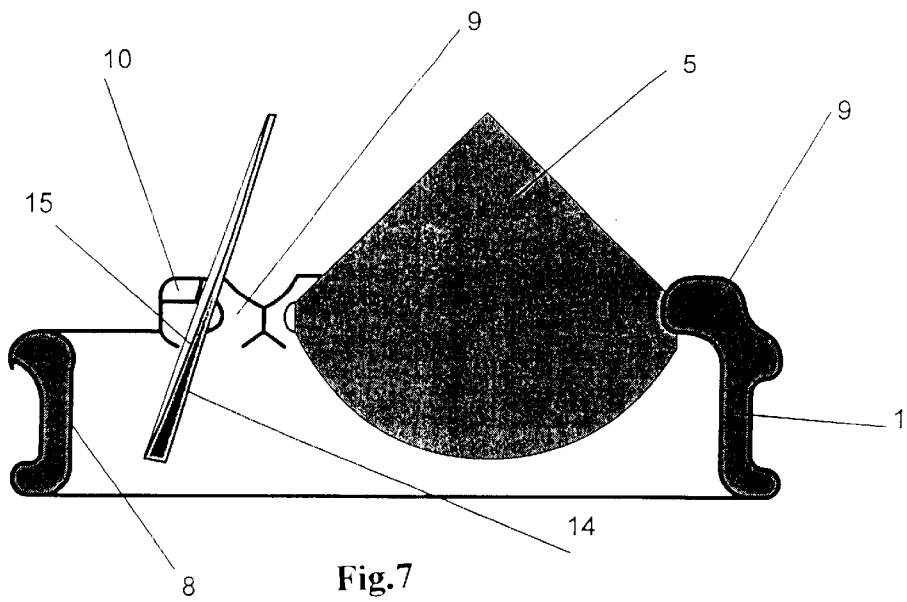
FIG. 7 is a tricuspid valve of the same view as valve with two flaps in FIG. 5.

The recesses for the bearings 6 can also be implemented in the form of a triad of blind holes being in communication via the lateral surfaces (FIG. 6), which is comprised of a central hole 18 and two side holes 19 and 20. The central hole is intended for mounting therein a flap bearing while two side holes—for the blood to be evacuated from a hinged area of the flap 4 and the body 1. The holes 19, 20 of the triad may have a lateral cylindrical surface with a smooth concave bottom. As a variant, they can be semispherical. Their lateral surface generally represents the surface of a body of revolution and the bottom is smoothly concave. And in the preferable embodiment a radius of the central hole 18 is greater than the radii of the side holes 19 and 20 and the depth of the central hole 18 exceeds that of the side holes 19 and 20. The longitudinally extending axes of each and every recess 7 are arranged in a plane which is perpendicular to a central line 21 of the valve (FIG. 2).

Figure 8:
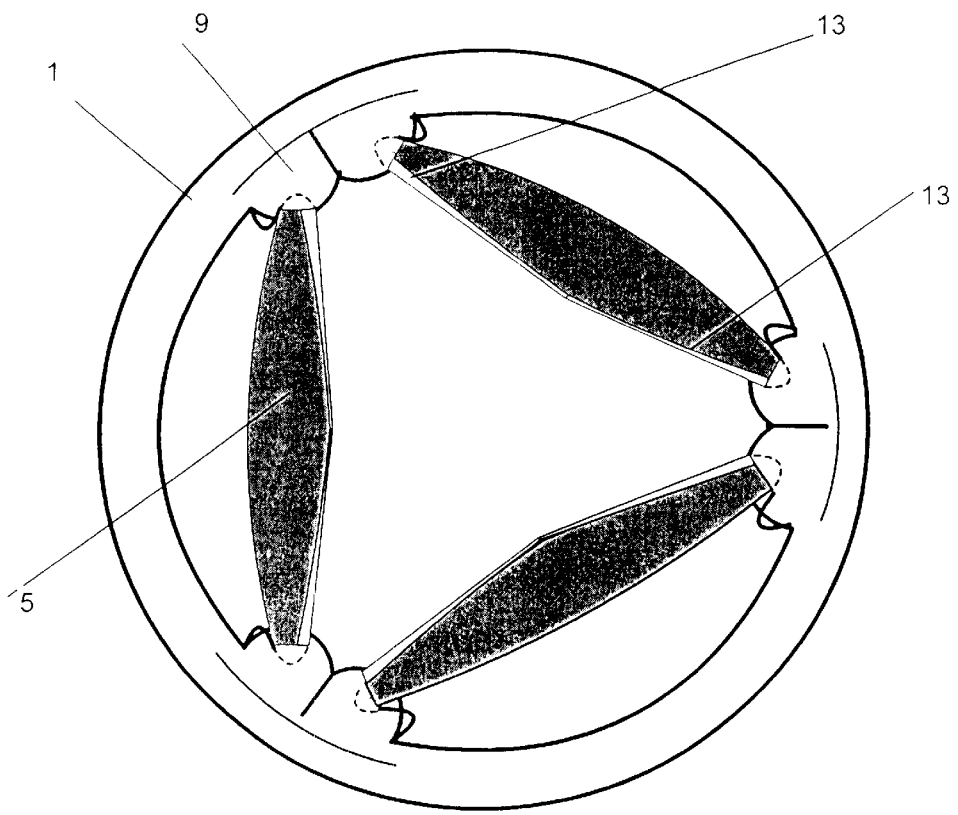
FIG. 8 is a plan view of a valve with three flaps.
Figure 9:
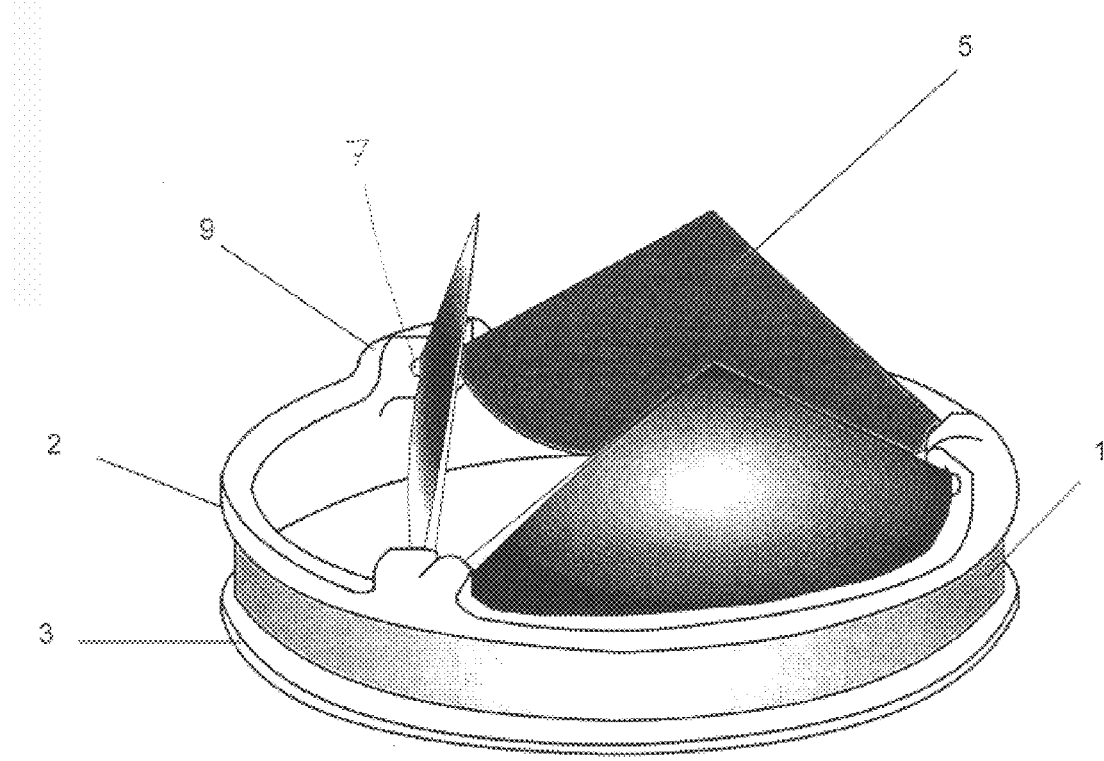
FIG. 9 shows the axonometric picture of a valve with three flaps.

In case of a closing element having three flaps 5, each one will have two joining edges 13 angularly converging towards the body's central axis and, along with this, axes of rotation of the flaps 5 will be arranged at an angle of 60° to form the sides of an equilateral triangle (FIG. 8).

The bearings 6 of flaps 4 and 5 have a spherical shape and can however, be implemented with a lateral cylindrical surface and end in, for example, a smooth convex spherical surface. The size of the bearings 6 of flaps 4 is selected such that they can be arranged with a clearance allowed in the recesses 7 of the annular body 1.

The embodiment of bearings and recesses, respectively, in the body with the presence of a lateral cylindrical surface and a smoothly concave bottom such that the longitudinal axis of each and every recess extends in a plane perpendicular to the central line of the prosthesis permits improving the washing of the surfaces of flap bearings and the annular body's recesses, using the blood, and also lowers a possibility of the flaps being forced out of the annular body by blood pressure.

Implementation of the rotation limiters of flaps in the form of four protrusions and their arrangement in pairs on the surface of the annular body, which is oriented towards a direct flow of blood i.e. taking them out of a hyperemic zone and a through hole of the prosthesis improves the washing of heart valve prosthesis elements, using the blood, and raises its hemodynamic efficiency.

Owing to implementation of two ledges on the surface of an annular body, facing the direct flow of blood, and arrangement on said ledges, of rotation limiters, the latter move even farther away from the blood hyperemic zone.

Imparting a W-shape to the ledges on an annular body contributes to reducing the prosthesis's blood-contacting surface in the region of the blood hyperemic zone.

Implementation of at least portion of the interior surface of an annular body with an inclination to the central axis of the prosthesis provides for an additional gap between the interior surface of the annular body and the side edge of a flap in the area of a blood hyperemic zone, owing to which fact a reverse restricted flow of blood arising in the prosthesis's closed position fully washes the surfaces of the flap rotation limiters.

Making the descending surface of each and every flap being flat and the ascending surface of each and every flap being spherically concave provides simultaneously an inseparable laminar flow of blood in-between the flaps, when these are open, and increases the moment of rotatable forces acting on a flap, a factor that contributes to more quickly closing and opening the flaps and also to fully opening them when the flaps are practically in parallel relation in the open position of the valve.

The heart valve prosthesis works in the following manner. With an excess pressure arising at the entry of the valve, the flaps 4 (or 5) interact by the bearings 6 with the recesses 7 of the annular body 1, rotate and open the valve, thus passing direct blood flow D therethrough. When completely opened, the flaps 4 or 5 are operatively engaged, at the side edges 11 thereof, with the rotation limiters 10 thereby to achieve the specified opening angle of the flaps 4 or 5.

With an excessive pressure arising at the exit of the valve the flaps 4 are rotated, when being operatively engaged by the bearings 6 with the recesses 7 of the annular body 1, and restrict reverse blood flow R through the valve while interacting by the side edges 11 with the interior surface 8 of the annular body 1 and by their joining edges 12. More, on account of the additional gaps between the bearings 6 of flaps 4 and the recesses 7 of annular body 1 as well as between the side edges 11 of flaps 4 and the inclined portions of the interior surface 8 of annular body 1 restricted reverse blood flow R washes the surfaces of the bearings 6 of flaps 4 and the surfaces of the rotation limiters 10.

INDUSTRIAL APPLICABILITY

The invention enables one to extend the lifetime of an implanted artificial cardiac valve by modifying its construction, which contributes to lowering thrombosis and blood cells hemolysis.

The technical result obtainable in using the present invention consists in providing a complete removal of blood from zones of cooperation of bearings with the surfaces of recesses, in which they move during the work process of a hinged joint "bearing—recess", when the flaps change their positions (from opening to closing and vice versa).

What is claimed is:

1. A heart valve prosthesis comprising an annular body with two flanges, and a closing element in the form of at least two flaps mounted through bearings into recesses of the body for rotation, the body having a constant height on a greater part of a ring circle, and ledges, the number of which is equal to that of the flaps, provided with rotation limiters of the flaps on a side facing a direct flow of blood, each flap having descending and ascending surfaces oriented to the direct and reverse flows of blood, respectively, a side edge and an edge for joining the other flap, characterized in that the descending surface of the flap, oriented towards the reverse flow of blood is flat while the ascending surface of the flap oriented towards the direct flow of blood is spherically concave, and the flap having a minimal thickness on an axis of symmetry at the joining edge.

2. The heart valve prosthesis according to claim 1, characterized in that the rotation limiters of the flaps are arranged on the ledges of a surface of the body, said ledges having a W-shape.

3. The heart valve prosthesis according to claim 2, characterized in that an interior surface of the ledges from the side of the direct flow of blood is inclined to a central line of the body.

4. The heart valve prosthesis according to claims 1 or 2, characterized in that recesses of the body have a lateral cylindrical surface and a concave bottom.

5. The heart valve prosthesis according to claim 1 or 2, characterized in that each recess for a bearing is in the form of a triad of blind holes being in communication, which is comprised of a central hole and two side holes.

6. The heart valve prosthesis according to claim 5, characterized in that a radius of the central hole is greater than the radii of the side holes.

7. The heart valve prosthesis according to claim 5, characterized in that the depth of the central hole is greater than that of the side holes.

8. The heart valve prosthesis according to claim 1, characterized in that a flange oriented to the direct flow of blood is thickened, recesses for bearings enter into the thickened flange and have a lateral cylindrical surface and the closing element is comprised of two flaps.

9. The heart valve prosthesis according to claim 1, characterized in that the closing element is comprised of three flaps, each having two joining edges angularly converging to a central axis of the body, and axes of rotation of the flaps extend at an angle of 60° one to another.

10. The heart valve prosthesis according to claim 1, characterized in that the annular body is made of pyrocarbon or titanium with a carbon-containing surface layer, in which a carbon content is gradually decreased from the surface into a depth of a material of the body.

\* \* \* \* \*